(12) United States Patent
Leyland-Jones et al.

(10) Patent No.: US 8,642,270 B2
(45) Date of Patent: Feb. 4, 2014

(54) PROGNOSTIC BIOMARKERS TO PREDICT OVERALL SURVIVAL AND METASTATIC DISEASE IN PATIENTS WITH TRIPLE NEGATIVE BREAST CANCER

(75) Inventors: Brian Leyland-Jones, Montréal (CA); Mark Abramovitz, Dollard-des-Ormeaux (CA)

(73) Assignee: VM Institute of Research, Montreal (CA)

( * ) Notice: Subject to any disclaimer, the term of this patent is extended or adjusted under 35 U.S.C. 154(b) by 497 days.

(21) Appl. No.: 12/702,049

(22) Filed: Feb. 8, 2010

(65) Prior Publication Data

US 2010/0210738 A1    Aug. 19, 2010

Related U.S. Application Data

(60) Provisional application No. 61/151,088, filed on Feb. 9, 2009.

(51) Int. Cl.
*C12Q 1/68*    (2006.01)
(52) U.S. Cl.
USPC ........................................ 435/6.14; 435/6.12
(58) Field of Classification Search
None
See application file for complete search history.

(56) References Cited

U.S. PATENT DOCUMENTS

2010/0292093 A1* 11/2010 Rubinstein ..................... 506/9
2011/0130296 A1*  6/2011 Benz et al. .................... 506/7

OTHER PUBLICATIONS

Bertucci et al (Int J Cancer, Apr. 2008, 123:236-240).*
ADAPT website, The Patterson Institute for Cancer Research, probesets for ANK3, printed Dec. 18, 2012.*
ADAPT website, The Patterson Institute for Cancer Research, probesets for CD24, printed Dec. 18, 2012.*
ADAPT website, The Patterson Institute for Cancer Research, probesets for ELF1, printed Dec. 18, 2012.*
ADAPT website, The Patterson Institute for Cancer Research, probesets for KLF6, printed Dec. 18, 2012.*
ADAPT website, The Patterson Institute for Cancer Research, probesets for KRAS, printed Dec. 18, 2012.*
ADAPT website, The Patterson Institute for Cancer Research, probesets for KRT1, printed Dec. 18, 2012.*
ADAPT website, The Patterson Institute for Cancer Research, probesets for MAP2K4, printed Dec. 18, 2012.*
ADAPT website, The Patterson Institute for Cancer Research, probesets for SDC4, printed Dec. 18, 2012.*
ADAPT website, The Patterson Institute for Cancer Research, probesets for SLC2A3, printed Dec. 18, 2012.*
ADAPT website, The Patterson Institute for Cancer Research, probesets for STK3, printed Dec. 18, 2012.*
ADAPT website, The Patterson Institute for Cancer Research, probesets for TFAP2C, printed Dec. 18, 2012.*
ADAPT website, The Patterson Institute for Cancer Research, probesets for WRN, printed Dec. 18, 2012.*
Abramovitz et al., Biotechniques 44(3):417-23 (2008).
Bibikova et al., Am J Pathol 165: 1799-1807 (2004).
Fan et al., Genome Res 14: 878-885 (2004).
Kreike et al., Breast Cancer Res 9: R65 (2007).
Sambrook et al., Molecular Cloning: A Laboratory Manual, 3rd Ed., Cold Spring Harbor Press, Cold Spring Harbor, NY (2001).

* cited by examiner

*Primary Examiner* — Laura B Goddard
(74) *Attorney, Agent, or Firm* — Benoît & Côté Inc.

(57) ABSTRACT

The present invention relates to a method for prognosing cancer in a subject with triple negative (TN) breast cancer, whose tumors lack expression of the estrogen receptor (ER), the progesterone receptor (PR) and normal (not amplified) levels of the human epidermal growth factor receptor 2 (HER2). Methods and biomarkers are disclosed that are useful for predicting the overall survival (OS) potential of cancer in a subject with triple negative breast cancer or for predicting metastatic disease in a subject with triple negative breast cancer. For example, the method comprises detecting in a sample from a subject one or more biomarkers selected from the group consisting of ANK3, CD24, EIF1, KLF6, KRAS, KRT1, MAP2K4, SDC4, SLC2A3, STK3, TFAP2C, and WRN. An increase or decrease in one or more biomarkers as compared to a standard is prognostic of OS of TN breast cancer. Likewise, in another example, the method comprises detecting in a sample from a subject one or more biomarkers selected from the group consisting of ANG, DICER1, EIF1, and MSH6. An increase or decrease in one or more biomarkers as compared to a standard is prognostic of metastasis of TN breast cancer.

7 Claims, 4 Drawing Sheets

SEQUENCE LISTING

<160> NUMBER OF SEQ ID NOS: 19

<210> SEQ ID NO 1
<211> LENGTH: 46
<212> TYPE: DNA
<213> ORGANISM: Artificial Sequence
<220> FEATURE:
<223> OTHER INFORMATION: Probe

<400> SEQUENCE: 1
atccctcact ttgggtccat gagaggaaaa gagagagaac tcattg         46

<210> SEQ ID NO 2
<211> LENGTH: 51
<212> TYPE: DNA
<213> ORGANISM: Artificial Sequence
<220> FEATURE:
<223> OTHER INFORMATION: Probe

<400> SEQUENCE: 2
caactatgga tcagaatagc cacatttaga acactttttg ttatcagtca a    51

<210> SEQ ID NO 3
<211> LENGTH: 46
<212> TYPE: DNA
<213> ORGANISM: Artificial Sequence
<220> FEATURE:
<223> OTHER INFORMATION: Probe

<400> SEQUENCE: 3
ttgccacaaa ggtctgttcg accagacata tcctagctaa gggatg         46

<210> SEQ ID NO 4
<211> LENGTH: 43
<212> TYPE: DNA
<213> ORGANISM: Artificial Sequence
<220> FEATURE:
<223> OTHER INFORMATION: Probe

<400> SEQUENCE: 4
ctgagggagc agagaggtgg atcctgtagg ctaaaggct tcc             43

<210> SEQ ID NO 5
<211> LENGTH: 45
<212> TYPE: DNA
<213> ORGANISM: Artificial Sequence
<220> FEATURE:
<223> OTHER INFORMATION: Probe

<400> SEQUENCE: 5
gcagacccag tatgaaatgg ggattattat agcaaccatt tggg           45

<210> SEQ ID NO 6
<211> LENGTH: 47
<212> TYPE: DNA
<213> ORGANISM: Artificial Sequence
<220> FEATURE:
<223> OTHER INFORMATION: Probe

<400> SEQUENCE: 6
ttcctctaag tgccagtatt cccagagttt tggttttga actagca         47

<210> SEQ ID NO 7
<211> LENGTH: 46
<212> TYPE: DNA
<213> ORGANISM: Artificial Sequence
<220> FEATURE:
<223> OTHER INFORMATION: Probe

<400> SEQUENCE: 7
gctctagttc tcccccagca tcactaacaa atatgcttgg caagac                46

<210> SEQ ID NO 8
<211> LENGTH: 47
<212> TYPE: DNA
<213> ORGANISM: Artificial Sequence
<220> FEATURE:
<223> OTHER INFORMATION: Probe

<400> SEQUENCE: 8
ccagcgtgag gtttgtttct accacttatt ccggagtaac cagataa               47

<210> SEQ ID NO 9
<211> LENGTH: 44
<212> TYPE: DNA
<213> ORGANISM: Artificial Sequence
<220> FEATURE:
<223> OTHER INFORMATION: Probe

<400> SEQUENCE: 9
ctgaaagaat agacccaagc gcatcacgac aaggatatga tgtc                  44

<210> SEQ ID NO 10
<211> LENGTH: 46
<212> TYPE: DNA
<213> ORGANISM: Artificial Sequence
<220> FEATURE:
<223> OTHER INFORMATION: Probe

<400> SEQUENCE: 10
gcctttctga aggcaagact gggattggat cacttcttaa acttcc                46

<210> SEQ ID NO 11
<211> LENGTH: 46
<212> TYPE: DNA
<213> ORGANISM: Artificial Sequence
<220> FEATURE:
<223> OTHER INFORMATION: Probe

<400> SEQUENCE: 11
ttggctgaaa aagctgtttc tggaatcacc cctagatctt tcttga                46

<210> SEQ ID NO 12
<211> LENGTH: 46
<212> TYPE: DNA
<213> ORGANISM: Artificial Sequence
<220> FEATURE:
<223> OTHER INFORMATION: Probe

<400> SEQUENCE: 12
tgctggagag gttaaggtgc aataagaatt tagggagaaa tgttgt                46

<210> SEQ ID NO 13
<211> LENGTH: 47
<212> TYPE: DNA
<213> ORGANISM: Artificial Sequence
<220> FEATURE:
<223> OTHER INFORMATION: Probe

```
<400> SEQUENCE: 13
catgcatgaa cccttcccta tgtccaaaaa cgttttcct gataact        47

<210> SEQ ID NO 14
<211> LENGTH: 45
<212> TYPE: DNA
<213> ORGANISM: Artificial Sequence
<220> FEATURE:
<223> OTHER INFORMATION: Probe

<400> SEQUENCE: 14
ctgctcagtc cctggaagat tgtcgctcct cagctctacg tctaa         45

<210> SEQ ID NO 15
<211> LENGTH: 47
<212> TYPE: DNA
<213> ORGANISM: Artificial Sequence
<220> FEATURE:
<223> OTHER INFORMATION: Probe

<400> SEQUENCE: 15
gctcactgta tttctgagtg ggggcatgat tttagggatt cattcag        47

<210> SEQ ID NO 16
<211> LENGTH: 48
<212> TYPE: DNA
<213> ORGANISM: Artificial Sequence
<220> FEATURE:
<223> OTHER INFORMATION: Probe

<400> SEQUENCE: 16
gcccaaagaa agagctacct ggacctttg ttttctgttt gacaacat        48

<210> SEQ ID NO 17
<211> LENGTH: 47
<212> TYPE: DNA
<213> ORGANISM: Artificial Sequence
<220> FEATURE:
<223> OTHER INFORMATION: Probe

<400> SEQUENCE: 17
tccatcatgt cctcgcattt tgggactaac tgcttccatt ttaaatg        47

<210> SEQ ID NO 18
<211> LENGTH: 46
<212> TYPE: DNA
<213> ORGANISM: Artificial Sequence
<220> FEATURE:
<223> OTHER INFORMATION: Probe

<400> SEQUENCE: 18
ttgccacaaa ggtctgttcg accagacata tcctagctaa gggatg         46

<210> SEQ ID NO 19
<211> LENGTH: 47
<212> TYPE: DNA
<213> ORGANISM: Artificial Sequence
<220> FEATURE:
<223> OTHER INFORMATION: Probe

<400> SEQUENCE: 19
tggtgaggag ggagatctgt aggatcatta ccaagggtac acagact        47
```

PROGNOSTIC BIOMARKERS TO PREDICT OVERALL SURVIVAL AND METASTATIC DISEASE IN PATIENTS WITH TRIPLE NEGATIVE BREAST CANCER

BACKGROUND (a) Field

The present invention relates to a method for prognosing or predicting overall survival (OS) or metastasis in a subject with triple negative (TN) breast cancer. More specifically, the invention relates to two sets of biomarkers, one set useful for prognosing or predicting OS in a subject with TN breast cancer and the other useful for prognosing or predicting metastasis in a subject with TN breast cancer.

(b) Related Prior Art

Tumor-associated antigens (TAAs) can help diagnose various tumors and sometimes determine the response to therapy or recurrence. An ideal tumor marker would be released only from tumor tissue, be specific for a given tumor type, be detectable at low levels of tumor cell burden, have a direct relationship to the tumor cell burden, and be present in all subjects with the tumor. However, although most tumors release detectable antigenic macromolecules into the circulation, no tumor marker has all the requisite characteristics to provide enough specificity or sensitivity to be used in early diagnosis or mass cancer screening programs.

Proteomic analyses of early stages cancers represent a new diagnostic tool for early detection of the disease. This technique evaluates the presence of various biomarkers in readily accessible body fluids such as serum, urine or saliva that are particular of specific changes in gene expression only occurring in cancer cells. Protein-based assays, such as the ELISA system, are used to evaluate the presence of biomarkers, therefore allowing detection and monitoring of cancer. The search for always more reliable cancer-related biomarkers is oriented towards proteins that are overexpressed, as a consequence of the disease process, and subsequently shed into body fluid. Novel proteomics methods and technologies are being used to discover new biomarkers for early-stage disease. Those methods comprise, besides the ELISA system, other antibody arrays, protein-based microarray technologies and multiplexed on-chip technologies. Despite their utility, there are several inherent disadvantages to these methods, such as the fact that they are often limited by the requirements for highly specific, high-affinity antibodies, two-site approaches and/or sensitive detection and signal amplification systems. Moreover, the development of proteomic pattern diagnostics is intricate since the specificity between physiologic biomarkers and the various types of cancer is hard to establish.

Breast cancer is the second most common cause of cancer-related mortality in Western women. One of the important challenges in current breast cancer research is to develop effective methods to determine whether a patient is likely to have a recurrence or progress to the aggressive, metastatic disease in order to aid clinicians in deciding the appropriate course of treatment. This is especially true for women with so called triple negative (TN) breast cancer. These tumors can be identified by the fact that they do not express the estrogen or progesterone receptors and express only normal (not amplified) levels of the human epidermal growth factor receptor 2 (HER2). However, it is currently impossible to predict the outcome of TN patients based solely on the pathological evaluation of the tumor.

Accordingly, novel methods of prognosis or classifying breast cancer subtypes are highly desirable.

SUMMARY

In accordance with the present invention there is provided a method for prognosing or predicting overall survival (OS) or predicting metastatic disease in a subject with TN breast cancer. More particularly, there is provided a 12 gene set predictor of OS listed in Table 1 that are particularly useful for prognosing or predicting OS in a subject with TN breast cancer. Also listed are probes that can be used in accordance with one embodiment of the present invention.

Furthermore and in accordance with another embodiment, there is provided a 4 gene set predictor of metastasis listed in Table 2 that are particularly useful for prognosing or predicting metastasis in a subject with TN breast cancer. Also listed are probes that can be used in accordance with one embodiment of the present invention.

TABLE 1

12 Gene Breast Cancer Set

| Gene Symbol | Accession No. | Probe Sequence | Sequence ID No. |
|---|---|---|---|
| ANK3 | NM_001149.2 | ATCCCTCACTTTGGGTCCATGAGAGGAAAAGAGAGAGAACTCATTG | 1 |
| CD24 | NM_013230.2 | CAACTATGGATCAGAATAGCCACATTTAGAACACTTTTTGTTATCAGTCAA | 2 |
| EIF1 | NM_005801.3 | TTGCCACAAAGGTCTGTTCGACCAGACATATCCTAGCTAAGGGATG | 3 |
| KLF6 | NM_001008490.1 | CTGAGGGAGCAGAGAGGTGGATCCTGTAGGCTAAAAGGCTTCC | 4 |
| KRAS | NM_033360.2 | GCAGACCCAGTATGAAATGGGGATTATTATAGCAACCATTTTGGG | 5 |
| KRAS | NM_033360.2 | TTCCTCTAAGTGCCAGTATTCCCAGAGTTTTGGTTTTTGAACTAGCA | 6 |
| KRT1 | NM_006121.2 | GCTCTAGTTCTCCCCCAGCATCACTAACAAATATGCTTGGCAAGAC | 7 |
| KRT1 | NM_006121.2 | CCAGCGTGAGGTTTGTTTCTACCACTTATTCCGGAGTAACCAGATAA | 8 |
| MAP2K4 | NM_003010.2 | CTGAAAGAATAGACCCAAGCGCATCACGACAAGGATATGATGTC | 9 |
| SDC4 | NM_002999.2 | GCCTTTCTGAAGGCAAGACTGGGATTGGATCACTTCTTAAACTTCC | 10 |
| SLC2A3 | NM_006931.1 | TTGGCTGAAAAAGCTGTTTCTGGAATCACCCCTAGATCTTTCTTGA | 11 |

TABLE 1-continued

12 Gene Breast Cancer Set

| Gene Symbol | Accession No. | Probe Sequence | Sequence ID No. |
|---|---|---|---|
| SLC2A3 | NM_006931.1 | TGCTGGAGAGGTTAAGGTGCAATAAGAATTTAGGGAGAAATGTTGT | 12 |
| STK3 | NM_006281.1 | CATGCATGAACCCTTCCCTATGTCCAAAAACGTTTTTCCTGATAACT | 13 |
| TFAP2C | NM_003222.2 | CTGCTCAGTCCCTGGAAGATTGTCGCTCCTCAGCTCTACGTCTAA | 14 |
| WRN | NM_000553.2 | GCTCACTGTATTTCTGAGTGGGGGCATGATTTTAGGGATTCATTCAG | 15 |

TABLE 2

4 Gene Breast Cancer Set

| Gene Symbol | Accession No. | Probe Sequence | Sequence ID No. |
|---|---|---|---|
| ANG | NM_001145.2 | GCCCAAAGAAAGAGCTACCTGGACCTTTTGTTTTCTGTTTGACAACAT | 16 |
| DICER1 | NM_030621.2 | TCCATCATGTCCTCGCATTTTGGGACTAACTGCTTCCATTTTAAATG | 17 |
| EIF1 | NM_005801.3 | TTGCCACAAAGGTCTGTTCGACCAGACATATCCTAGCTAAGGGATG | 18 |
| MSH6 | NM_000179.1 | TGGTGAGGAGGGAGATCTGTAGGATCATTACCAAGGGTACACAGACT | 19 |

Provided is a method of predicting the OS potential of a TN breast cancer in a subject. Specifically, the method comprises detecting in a sample from the subject one or more biomarkers selected from the group consisting of ANK3, CD24, EIF1, KLF6, KRAS, KRT1, MAP2K4, SDC4, SLC2A3, STK3, TFAP2C, and WRN (Table 1). An increase or decrease in one or more of the biomarkers indicates a breast cancer that is prone to good or poor OS. The sample can, for example, comprise TN breast tumor tissue.

Also provided is a method of predicting the metastatic potential of a TN breast cancer in a subject. Specifically, the method comprises detecting in a sample from the subject one or more biomarkers selected from the group consisting of ANG, DICER1, EIF1, and MSH6 (Table 2). An increase or decrease in one or more of the biomarkers indicates a breast cancer that is prone or not prone to metastatic disease. The sample can, for example, comprise TN breast tumor tissue.

Also provided is a method of treating a subject with TN breast cancer that comprises modifying the treatment regimen of the subject based on the results of the method of predicting the recurrence potential of a TN breast cancer in a subject. The treatment regiment is modified to be aggressive based on an increase in one or more biomarkers selected from the group consisting of ANK3, CD24, EIF1, KLF6, KRAS, KRT1, MAP2K4, SDC4, SLC2A3, STK3, TFAP2C, and WRN as compared to a standard, and a decrease in one or more biomarkers selected from a group consisting of ANK3, CD24, EIF1, KLF6, KRAS, KRT1, MAP2K4, SDC4, SLC2A3, STK3, TFAP2C, and WRN as compared to a standard.

Also provided is a method of treating a subject with TN breast cancer that comprises modifying the treatment regimen of the subject based on the results of the method of predicting the recurrence potential of a TN breast cancer in a subject. The treatment regiment is modified to be aggressive based on an increase in one or more biomarkers selected from the group consisting of ANG, DICER1, EIF1, and MSH6 as compared to a standard, and a decrease in one or more biomarkers selected from a group consisting of ANG, DICER1, EIF1, and MSH6 as compared to a standard.

Another aspect of the invention is to use the one or more biomarkers selected from the group consisting of ANK3, CD24, EIF1, KLF6, KRAS, KRT1, MAP2K4, SDC4, SLC2A3, STK3, TFAP2C, and WRN for predicting the OS potential of a TN breast cancer in a subject.

Another aspect of the invention is to use the one or more biomarkers selected from the group consisting of ANG, DICER1, EIF1, and MSH6 for predicting the metastatic potential of a TN breast cancer in a subject.

Another aspect of the invention is to use an increase in one or more biomarkers selected from the group consisting of ANK3, CD24, EIF1, KLF6, KRAS, KRT1, MAP2K4, SDC4, SLC2A3, STK3, TFAP2C, and WRN as compared to a standard, and a decrease in one or more biomarkers selected from a group consisting of ANK3, CD24, EIF1, KLF6, KRAS, KRT1, MAP2K4, SDC4, SLC2A3, STK3, TFAP2C, and WRN as compared to a standard, to modify a treatment regimen of a subject with TN breast cancer. The treatment regimen is modified to be aggressive based on the increase or decrease measured.

Another aspect of the invention is to use an increase in one or more biomarkers selected from the group consisting of ANG, DICER1, EIF1, and MSH6 as compared to a standard, and a decrease in one or more biomarkers selected from a group consisting of ANG, DICER1, EIF1, and MSH6 as compared to a standard, to modify a treatment regimen of a subject with TN breast cancer. The treatment regimen is modified to be aggressive based on the increase or decrease measured.

Also provided is a kit comprising primers to detect the expression of biomarkers selected from the group consisting of ANK3, CD24, EIF1, KLF6, KRAS, KRT1, MAP2K4, SDC4, SLC2A3, STK3, TFAP2C, and WRN or primers to detect the expression of biomarkers selected from the group consisting of ANG, DICER1, EIF1, and MSH6.

Other features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

DETAILED DESCRIPTION

This invention relates to a for predicting the OS or metastatic potential of a TN breast cancer in a subject, which comprises determining the expression of at least one gene chosen from the list of genes of Table 1 and/or Table 2 (above) in a subject sample.

The term "biomarker" as used herein refers to a gene that is differentially expressed in individuals with breast cancer and is predictive of different tumor types, tumor responsiveness or survival outcomes. The term "biomarker" includes one or more of the genes listed in any of Tables 1 and 2.

Accordingly, one aspect of the invention is a method of prognosing or classifying breast cancer subtypes in a subject, comprising the steps of determining the expression of a biomarker in a test sample from the subject, wherein the biomarker comprises one or more biomarkers as shown in any of Tables 1 and 2 and comparing the expression of the biomarker with a control representative of various cancer subtypes, wherein a difference in the expression of the biomarker between the control and the test sample is used to prognose or classify the subject with a breast cancer subtype.

The phrase "prognosing or classifying" as used herein refers to a method or process of determining whether a subject has a specific tumor subtype based on biomarker expression profiles.

The term "test sample" as used herein refers to any fluid, cell or tissue sample from a subject which can be assayed for biomarker expression products, particularly genes differentially expressed in subjects with different forms of breast cancer subtypes. In one embodiment, the test sample is a cell, cells or tissue from a tumor biopsy from the subject.

The preferred test sample to test using the cancer panel consists in obtaining FFPE tumor blocks in 5×5 µm sections by subject, each section being incorporated in a sterile 1.5 ml Eppendorf™ tube. Moreover, one 5 µm section of tumor sample on a slide by subject may be used for haematoxylin and eosin (H&E) staining.

As used herein, the terms "control" and "standard" refer to a specific value that one can use to prognose or classify the value obtained from the sample. In one embodiment, a dataset may be obtained from samples from a group of subjects known to have a particular breast cancer type or subtype. The expression data of the biomarkers in the dataset can be used to create a control (standard) value that is used in testing samples from new subjects. In such an embodiment, the "control" or "standard" is a predetermined value for each biomarker or set of biomarkers obtained from subjects with breast cancer subjects whose biomarker expression values and tumor types are known.

In another embodiment, the control or standard can be an actual control or standard sample from a subject with a known TN breast cancer subtype.

The term "differentially expressed" or "differential expression" as used herein refers to a difference in the level of expression of the biomarkers that can be assayed by measuring the level of expression of the products of the biomarkers, such as the difference in level of messenger RNA transcript expressed or proteins expressed of the biomarkers. In a preferred embodiment, the difference is statistically significant. The term "difference in the level of expression" refers to an increase or decrease in the measurable expression level of a given biomarker as measured by the amount of messenger RNA transcript and/or the amount of protein in a sample as compared with the measurable expression level of a given biomarker in a control. In one embodiment, the differential expression can be compared using the ratio of the level of expression of a given biomarker or biomarkers as compared with the expression level of the given biomarker or biomarkers of a control, wherein the ratio is not equal to 1.0. For example, an RNA or protein is differentially expressed if the ratio of the level of expression in a first sample as compared with a second sample is greater than or less than 1.0. For example, a ratio of greater than 1, 1.2, 1.5, 1.7, 2, 3, 3, 5, 10, 15, 20 or more, or a ratio less than 1, 0.8, 0.6, 0.4, 0.2, 0.1, 0.05, 0.001 or less. In another embodiment the differential expression is measured using p-value. For instance, when using p-value, a biomarker is identified as being differentially expressed as between a first sample and a second sample when the p-value is less than 0.1, preferably less than 0.05, more preferably less than 0.01, even more preferably less than 0.005, the most preferably less than 0.001.

In another embodiment, expression data from multiple biomarkers is analyzed using cluster techniques. In one embodiment, clustering is based on correlation of average normalized signal intensities. In one embodiment, the biomarkers comprise the biomarkers listed in Table 1 and/or Table 2.

The phrase "determining the expression of biomarkers" as used herein refers to determining or quantifying RNA or proteins expressed by the biomarkers. The term "RNA" includes mRNA transcripts, and/or specific spliced variants of mRNA. The term "RNA product of the biomarker" as used herein refers to RNA transcripts transcribed from the biomarkers and/or specific spliced variants. In the case of "protein", it refers to proteins translated from the RNA transcripts transcribed from the biomarkers. The term "protein product of the biomarker" refers to proteins translated from RNA products of the biomarkers.

A person skilled in the art will appreciate that a number of methods can be used to detect or quantify the level of RNA products of the biomarkers within a sample, including microarrays, RT-PCR (including quantitative RT-PCR), nuclease protection assays and Northern blot analyses. In one embodiment, the assay used is a DASL assay as shown in Example 1 which uses a bead-array format.

In addition, a person skilled in the art will appreciate that a number of methods can be used to determine the amount of a protein product of a biomarker of the invention, including immunoassays such as Western blots, ELISA, and immunoprecipitation followed by SDS-PAGE and immunocytochemistry.

Conventional techniques of molecular biology, microbiology and recombinant DNA techniques, are within the skill of the art. Such techniques are explained fully in the literature. See, e.g., Sambrook, Fritsch & Maniatis, 1989, Molecular Cloning: A Laboratory Manual, Second Edition; Oligonucleotide Synthesis (M. J. Gait, ed., 1984); Nucleic Acid Hybridization (B. D. Harnes & S. J. Higgins, eds., 1984); A Practical Guide to Molecular Cloning (B. Perbal, 1984); and a series, Methods in Enzymology (Academic Press, Inc.); Short Protocols In Molecular Biology, (Ausubel et al., ed., 1995).

A person skilled in the art will appreciate that a number of detection agents can be used to determine the expression of the biomarkers. For example, to detect RNA products of the biomarkers, probes, primers, complementary nucleotide sequences or nucleotide sequences that hybridize to the RNA products can be used. To detect protein products of the biomarkers, ligands or antibodies that specifically bind to the protein products can be used.

The term "nucleic acid" includes DNA and RNA and can be either double stranded or single stranded.

The term "hybridize" refers to the sequence specific non-covalent binding interaction with a complementary nucleic acid. In a preferred embodiment, the hybridization is under high stringency conditions. Appropriate stringency conditions which promote hybridization are known to those skilled in the art, or can be found in Current Protocols in Molecular Biology, John Wiley & Sons, N.Y. (1989), 6.3.1 6.3.6. For example, 6.0× sodium chloride/sodium citrate (SSC) at about 45° C., followed by a wash of 2.0×SSC at 50° C. may be employed.

The term "primer" as used herein refers to a nucleic acid sequence, whether occurring naturally as in a purified restriction digest or produced synthetically, which is capable of acting as a point of synthesis of when placed under conditions in which synthesis of a primer extension product, which is complementary to a nucleic acid strand is induced (e.g. in the presence of nucleotides and an inducing agent such as DNA polymerase and at a suitable temperature and pH). The primer must be sufficiently long to prime the synthesis of the desired extension product in the presence of the inducing agent. The exact length of the primer will depend upon factors, including temperature, sequences of the primer and the methods used. A primer typically contains 15-25 or more nucleotides, although it can contain less. The factors involved in determining the appropriate length of primer are readily known to one of ordinary skill in the art. The term "primer" as used herein refers to a set of primers which can produce a double stranded nucleic acid product complementary to a portion of the RNA products of the biomarker or sequences complementary thereof.

The term "probe" as used herein refers to a nucleic acid sequence that will hybridize to a nucleic acid target sequence. In one example, the probe hybridizes to an RNA product of the biomarker or a nucleic acid sequence complementary thereof. The length of probe depends on the hybridize conditions and the sequences of the probe and nucleic acid target sequence. In one embodiment, the probe is at least 8, 10, 15, 20, 25, 50, 75, 100, 150, 200, 250, 400, 500 or more nucleotides in length. In a preferred embodiment, the assay used is a DASL assay and the probes used are those identified in Table 1. The probe sequences are the oligo sequence on the 5' and 3' end which is then extended and ligated to form the "probe" sequence.

The term "antibody" as used herein is intended to include monoclonal antibodies, polyclonal antibodies, and chimeric antibodies. The antibody may be from recombinant sources and/or produced in transgenic animals. The term "antibody fragment" as used herein is intended to include Fab, Fab', F(ab')2, scFv, dsFv, ds-scFv, dimers, minibodies, diabodies, and multimers thereof and bispecific antibody fragments. Antibodies can be fragmented using conventional techniques. For example, F(ab')2 fragments can be generated by treating the antibody with pepsin. The resulting F(ab')2 fragment can be treated to reduce disulfide bridges to produce Fab' fragments. Papain digestion can lead to the formation of Fab fragments. Fab, Fab' and F(ab')2, scFv, dsFv, ds-scFv, dimers, minibodies, diabodies, bispecific antibody fragments and other fragments can also be synthesized by recombinant techniques.

Antibodies having specificity for a specific protein, such as the protein product of a biomarker, may be prepared by conventional methods. A mammal, (e.g. a mouse, hamster, or rabbit) can be immunized with an immunogenic form of the peptide which elicits an antibody response in the mammal. Techniques for conferring immunogenicity on a peptide include conjugation to carriers or other techniques well known in the art. For example, the peptide can be administered in the presence of adjuvant. The progress of immunization can be monitored by detection of antibody titers in plasma or serum. Standard ELISA or other immunoassay procedures can be used with the immunogen as antigen to assess the levels of antibodies. Following immunization, antisera can be obtained and, if desired, polyclonal antibodies isolated from the sera.

To produce monoclonal antibodies, antibody producing cells (lymphocytes) can be harvested from an immunized animal and fused with myeloma cells by standard somatic cell fusion procedures thus immortalizing these cells and yielding hybridoma cells. Such techniques are well known in the art, (e.g. the hybridoma technique originally developed by Kohler and Milstein (Nature 256:495-497 (1975)) as well as other techniques such as the human B-cell hybridoma technique (Kozbor et al., Immunol. Today 4:72 (1983)), the EBV-hybridoma technique to produce human monoclonal antibodies (Cole et al., Methods Enzymol, 121:140-67 (1986)), and screening of combinatorial antibody libraries (Huse et al., Science 246:1275 (1989)). Hybridoma cells can be screened immunochemically for production of antibodies specifically reactive with the peptide and the monoclonal antibodies can be isolated.

A person skilled in the art will appreciate that the detection agents can be labeled.

The label is preferably capable of producing, either directly or indirectly, a detectable signal. For example, the label may be radio-opaque or a radioisotope, such as 3H, 14C, 32P, 35S, 123I, 125I, 131I; a fluorescent (fluorophore) or chemiluminescent (chromophore) compound, such as fluorescein isothiocyanate, rhodamine or luciferin; an enzyme, such as alkaline phosphatase, beta-galactosidase or horseradish peroxidase; an imaging agent; or a metal ion.

Accordingly, the invention includes a kit for prognosing or classifying cancer subtypes in a subject with breast cancer, comprising at least one detection agent that can detect the expression products of biomarkers, wherein the biomarkers comprise at least one biomarker as shown in Table 1.

The kit can also include a control or reference standard and/or instructions for use thereof. In addition, the kit can include ancillary agents such as vessels for storing or transporting the detection agents and/or buffers or stabilizers.

The term "subject" as used herein refers to any member of the animal kingdom, preferably a human being that has breast cancer.

Described herein are methods for predicting the OS or metastatic potential of a TN breast cancer in a subject. The methods comprises detecting in a sample from a subject one or more biomarkers selected from the group consisting of ANK3, CD24, EIF1, KLF6, KRAS, KRT1, MAP2K4, SDC4, SLC2A3, STK3, TFAP2C, and WRN. An increase or decrease in one or more of the biomarkers as compared to a standard indicates a TN breast cancer that is prone to recur. Optionally, the sample comprises TN breast tumor tissue.

The method also comprises detecting in a sample from a subject one or more biomarkers selected from the group consisting of ANG, DICER1, EIF1, and MSH6. An increase or decrease in one or more of the biomarkers as compared to a standard indicates a TN breast cancer that is prone to metastasis. Optionally, the sample comprises TN breast tumor tissue.

Optionally, multiple biomarkers are detected. Detection can comprise identifying an RNA expression pattern. An increase in one or more of the biomarkers selected from the group consisting of ANK3, CD24, EIF1, KLF6, KRAS, KRT1, MAP2K4, SDC4, SLC2A3, STK3, TFAP2C, and WRN as compared to a standard indicates a TN breast cancer that has a good OS potential. A decrease in one or more of the biomarkers selected from the group consisting of ANK3, CD24, EIF1, KLF6, KRAS, KRT1, MAP2K4, SDC4, SLC2A3, STK3, TFAP2C, and WRN as compared to a standard indicates a TN breast cancer that has a poor OS potential. Optionally, the detected biomarkers comprise two or more, three or more, four or more, five or more, six or more, seven or more, etc. or all 12 biomarkers selected from the group consisting of ANK3, CD24, EIF1, KLF6, KRAS, KRT1, MAP2K4, SDC4, SLC2A3, STK3, TFAP2C, and WRN. For example, the detected biomarkers can comprise ANK3, CD24. Alternatively, the detected biomarkers can comprise TFAP2C, and WRN. For example, the detected biomarkers can comprise ANK3, CD24, and EIF1. Alternatively, the detected biomarkers can comprise STK3, TFAP2C, and WRN. For example, the detected biomarkers can comprise ANK3, CD24, EIF1, and KLF6. Alternatively, the detected biomarkers can comprise SLC2A3, STK3, TFAP2C, and WRN. For example, the selected biomarkers can comprise ANK3, CD24, EIF1, KLF6, and KRAS. Alternatively, the selected biomarkers can comprise SDC4, SLC2A3, STK3, TFAP2C, and WRN. For example, the selected biomarkers can comprise ANK3, CD24, EIF1, KLF6, KRAS, and KRT1. Alternatively, the selected biomarkers can comprise SDC4, SLC2A3, STK3, TFAP2C, and WRN. For example, the selected biomarkers can comprise ANK3, CD24, EIF1, KLF6, KRAS, KRT1, and MAP2K4. Optionally, the selected biomarkers comprise biomarkers selected from the group consisting of KRT1, MAP2K4, SDC4, SLC2A3, STK3, TFAP2C, and WRN.

In addition, optionally, multiple biomarkers are detected. Detection can comprise identifying an RNA expression pattern. An increase in one or more of the biomarkers selected from the group consisting of ANG, DICER1, EIF1, and MSH6 as compared to a standard indicates a TN breast cancer that has a low metastatic disease potential. A decrease in one or more of the biomarkers selected from the group consisting of ANG, DICER1, EIF1, and MSH6 as compared to a standard indicates a TN breast cancer that has a high metastatic disease potential. Optionally, the detected biomarkers comprise two or more, three or more, or all 4 biomarkers selected from the group consisting of ANG, DICER1, EIF1, and MSH6. For example, the detected biomarkers can comprise ANG, and DICER1. Alternatively, the detected biomarkers can comprise EIF1, and MSH6. For example, the detected biomarkers can comprise ANG, DICER1, and EIF1. Alternatively, the detected biomarkers can comprise DICER1, EIF1, and MSH6.

Optionally, the detecting step comprises detecting mRNA levels of the biomarker. The mRNA detection can, for example, comprise reverse-transcription polymerase chain reaction (RT-PCR), real-time quantitative PCR (RT-qPCR), Northern analysis, microarray analysis, and cDNA-mediated annealing, selection, extension, and ligation (DASL®) assay (Illumina, Inc.; San Diego, Calif.). Preferably, the RNA detection comprises the cDNA-mediated annealing, selection, extension, and ligation (DASL®) assay (Illumina, Inc.). Optionally, the detecting step comprises detecting mRNA levels of the biomarker. The analytical techniques used to determine mRNA expression are known. See, e.g., Sambrook et al., Molecular Cloning: A Laboratory Manual, 3rd Ed., Cold Spring Harbor Press, Cold Spring Harbor, N.Y. (2001).

Comparing the mRNA biomarker content with a biomarker standard includes comparing mRNA content from the subject with the mRNA content of a biomarker standard. Such comparisons can be comparisons of the presence, absence, relative abundance, or combination thereof of specific mRNA molecules in the sample and the standard. Many of the analytical techniques discussed above can be used alone or in combination to provide information about the mRNA content (including presence, absence, and/or relative abundance information) for comparison to a biomarker standard. For example, the DASL® assay can be used to establish a mRNA profile for a sample from a subject and the abundances of specific identified molecules can be compared to the abundances of the same molecules in the biomarker standard.

Optionally, the detecting step comprises detecting the protein expression levels of the biomarker. The protein detection can, for example, comprise an assay selected from the group consisting of Western blot, enzyme-linked immunosorbent assay (ELISA), enzyme immunoassay (EIA), radioimmunoassay (RIA), immunohistochemistry, and protein array. The analytical techniques used to determine protein expression are known. See, e.g., Sambrook et al., Molecular Cloning: A Laboratory Manual, 3rd Ed., Cold Spring Harbor Press, Cold Spring Harbor, N.Y. (2001).

Biomarker standards can be predetermined, determined concurrently, or determined after a sample is obtained from the subject. Biomarker standards for use with the methods described herein can, for example, include data from samples from subjects without TN breast cancer, data from samples from subjects with TN breast cancer that is not a progressive, recurrent, and/or metastatic TN breast cancer, and data from samples from subjects with TN breast cancer that is a progressive, recurrent, and/or metastatic TN breast cancer. Comparisons can be made to as multiple biomarker standards. The standards can be run in the same assay or can be known standards from a previous assay.

Also provided herein is a method of treating a subject with TN breast cancer. The method comprises modifying a treatment regimen of the subject based on the results of any of the methods of predicting the recurrence, progression, OS and metastatic potential of a TN breast cancer in a subject. Optionally, the treatment regimen is modified to be aggressive based on an increase in one or more biomarkers selected from the group consisting of ANK3, CD24, EIF1, KLF6, KRAS, KRT1, MAP2K4, SDC4, SLC2A3, STK3, TFAP2C, and WRN as compared to a standard or ANG, DICER1, EIF1, and MSH6 as compared to a standard. Optionally, the treatment regimen is modified to be aggressive based on a decrease in one or more biomarkers selected from the group consisting of ANK3, CD24, EIF1, KLF6, KRAS, KRT1, MAP2K4, SDC4, SLC2A3, STK3, TFAP2C, and WRN as compared to a standard. Optionally, the treatment regimen is modified to be aggressive based on a combination of an increase in one or more biomarkers selected from the group consisting of ANK3, CD24, EIF1, KLF6, KRAS, KRT1, MAP2K4, SDC4, SLC2A3, STK3, TFAP2C, and WRN or ANG, DICER1, EIF1, and MSH6 and a decrease in one or more biomarkers selected from the group consisting of ANK3, CD24, EIF1, KLF6, KRAS, KRT1, MAP2K4, SDC4, SLC2A3, STK3, TFAP2C, and WRN or ANG, DICER1, EIF1, and MSH6 as compared to a standard.

Also provided is a kit comprising primers to detect the expression of biomarkers selected from the group consisting of ANK3, CD24, EIF1, KLF6, KRAS, KRT1, MAP2K4, SDC4, SLC2A3, STK3, TFAP2C, and WRN or ANG, DICER1, EIF1, and MSH6. Optionally, directions to use the primers provided in the kit to predict the OS potential of TN breast cancer or metastasis of TN breast cancer in a subject, materials needed to obtain RNA in a sample from a subject, containers for the primers, or reaction vessels are included in the kit.

As used herein, subject can be a vertebrate, more specifically a mammal (e.g., a human, horse, cat, dog, cow, pig, sheep, goat mouse, rabbit, rat, and guinea pig), birds, reptiles, amphibians, fish, and any other animal. The term does not denote a particular age. Thus, adult and newborn subjects are intended to be covered. As used herein, patient or subject may be used interchangeably and can refer to a subject afflicted with a disease or disorder (e.g. breast cancer). The term patient or subject includes human and veterinary subjects.

As used herein, the terms treatment, treat, or treating refers to a method of reducing the effects of a disease or condition or symptom of the disease or condition. Thus, in the disclosed method, treatment can refer to a 10%, 20%, 30%, 40%, 50%, 60%, 70%, 80%, 90%, or 100% reduction in the severity of an established disease or condition or symptom of the disease or condition. For example, a method of treating a disease is considered to be a treatment if there is a 10% reduction in one or more symptoms of the disease in a subject as compared to a control. Thus, the reduction can be a 10%, 20%, 30%, 40%, 50%, 60%, 70%, 80%, 90%, 100% or any percent reduction between 10 and 100% as compared to native or control levels. It is understood that treatment does not necessarily refer to a cure or complete ablation of the disease, condition, or symptoms of the disease or condition.

Disclosed are materials, compositions, and components that can be used for, can be used in conjunction with, can be used in preparation for, or are products of the disclosed methods and compositions. These and other materials are disclosed herein, and it is understood that when combinations, subsets, interactions, groups, etc. of these materials are disclosed that while specific reference of each various individual and collective combinations and permutations of these compounds may not be explicitly disclosed, each is specifically contemplated and described herein. For example, if a method is disclosed and discussed and a number of modifications that can be made to a number of molecules including the method are discussed, each and every combination and permutation of the method, and the modifications that are possible are specifically contemplated unless specifically indicated to the contrary. Likewise, any subset or combination of these is also specifically contemplated and disclosed. This concept applies to all aspects of this disclosure including, but not limited to, steps in methods using the disclosed compositions. Thus, if there are a variety of additional steps that can be performed, it is understood that each of these additional steps can be performed with any specific method steps or combination of method steps of the disclosed methods, and that each such combination or subset of combinations is specifically contemplated and should be considered disclosed.

Publications cited herein and the material for which they are cited are hereby specifically incorporated by reference in their entireties.

The above disclosure generally describes the present invention. A more complete understanding can be obtained by reference to the following specific examples. These examples are described solely for the purpose of illustration and are not intended to limit the scope of the invention. Changes in form and substitution of equivalents are contemplated as circumstances might suggest or render expedient. Although specific terms have been employed herein, such terms are intended in a descriptive sense and not for purposes of limitation. The following non-limiting examples are illustrative of the present invention:

EXAMPLE 1

RNA Isolation

RNA is isolated from formalin-fixed paraffin-embedded (FFPE) tissue according to the methods described in Abramovitz et al., Biotechniques, 44 (3):417-23 (2008). In brief, three 5 m sections per block were cut and placed into a 1.5 mL sterile microfuge tube. The tissue section was deparaffinized with 100% xylene for 3 minutes at 50° C. The tissue section was centrifuged, washed twice with ethanol, and allowed to air dry. The tissue section was digested with Proteinase K for 24 hours at 50° C. RNA was isolated using an Ambion Recover All Kit® (Ambion®; Austin, Tex.).

cDNA-Mediated Annealing, Selection, Extension, and Ligation Assay (DASL® Assay)

Upon the completion of RNA isolation, the isolated RNA is used in the DASL® assay. The DASL® assay is performed according to the protocols supplied by the manufacturer (Illumina®, Inc.; San Diego, Calif.). The probe sequences for the thirty-one biomarker genes are contained within Table 1.

EXAMPLE 2

Identification of a 12 Gene Set that can be Used to Sub Classify TN Breast Tumors Predictors for the OS Potential of TN Breast Cancer The predictive set of 512 genes were optimized for performance in the cDNA-mediated annealing, selection, extension, and ligation (DASL®) assay (Illumina®, Inc.; San Diego, Calif.). The DASL® assay is based upon multiplexed reverse transcription-polymerase chain reaction (RT-PCR)

applied in a microarray format and enables the quantitation of expression of up to 1536 probes using RNA isolated from archived formalin-fixed paraffin embedded (FFPE) tumor tissue samples in a high throughput format (Bibikova et al., Am. J. Pathol., 165:1799-807 (2004); Fan et al., Genome Res., 14:878-85 (2004)). RNA was isolated from tumor samples from patients with TN breast cancer and was analyzed using the DASL® assay. Here, in a sample size of 63, Cox regression analysis yielded 15 probes from 12 unique genes prognostic of overall survival (FDR<5%). These genes include ANK3, CD24, EIF1, KLF6, KRAS, KRT1, MAP2K4, SDC4, SLC2A3, STK3, TFAP2C, and WRN. Specific probes and the weight determined by each probes are disclosed in appendix 1.

APPENDIX 1

Summary of Mortality Events in Good and Poor Prognosis Cohorts

| Group | Total N | N of Events | Censored N | Percent |
|---|---|---|---|---|
| Poor Prognosis | 32 | 11 | 21 | 65.6% |
| Good Prognosis | 31 | 2 | 29 | 93.5% |
| Overall | 63 | 13 | 50 | 79.4% |

Figure 1:
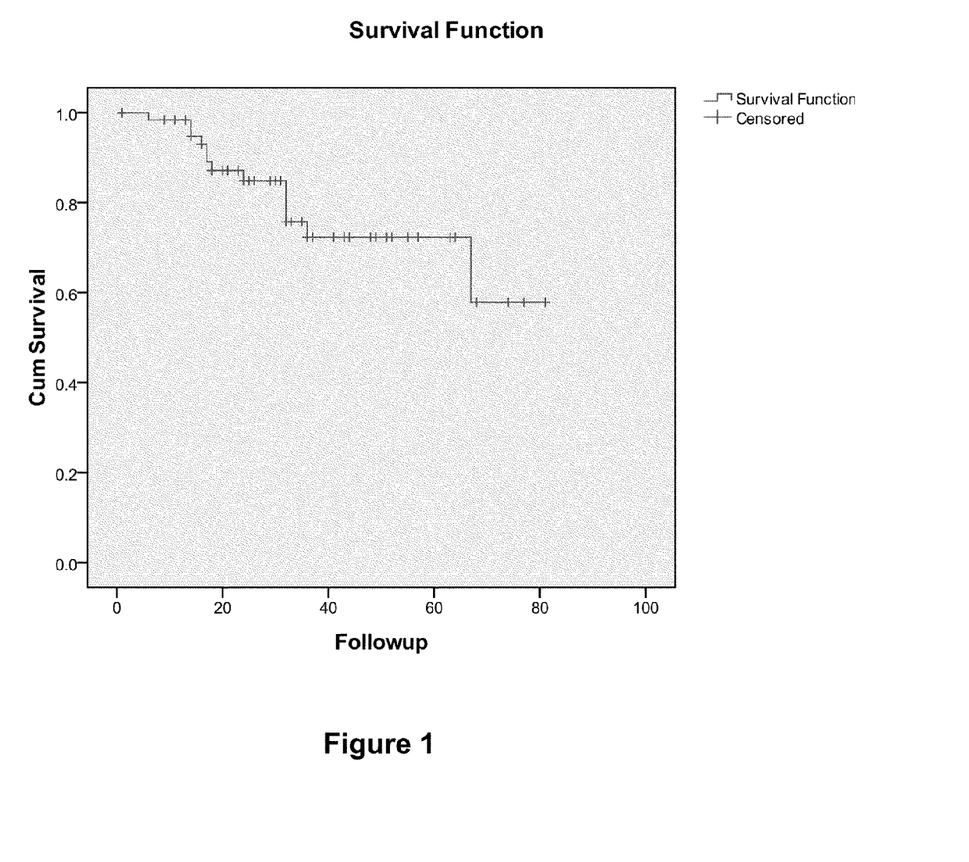
FIG. 1 shows Kaplan Meier Survival Analysis for the 63 TN Patient Cohort. Follow-up time is in months and cumulative survival is based on a percentage of the entire cohort (n=63).
Figure 2:
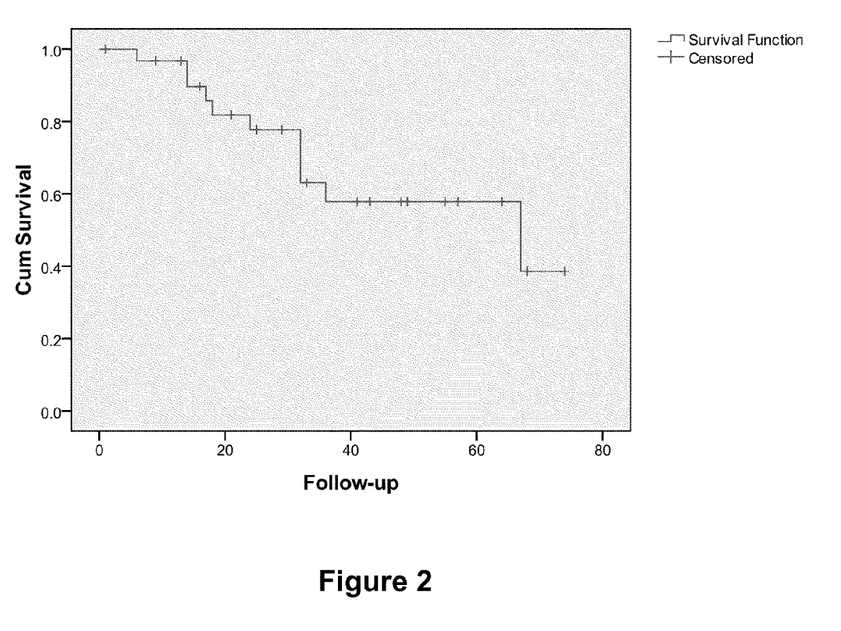
FIG. 2 shows Kaplan-Meier analysis of the poor prognosis group. Follow-up time is in months and the cumulative survival function is based upon censored data for the patient population with adequate follow-up time for 32 patients with a poor prognosis as determined from their score based upon 15 markers as described in "Methods for determination of overall survival (OS) prognostics"
Figure 3:
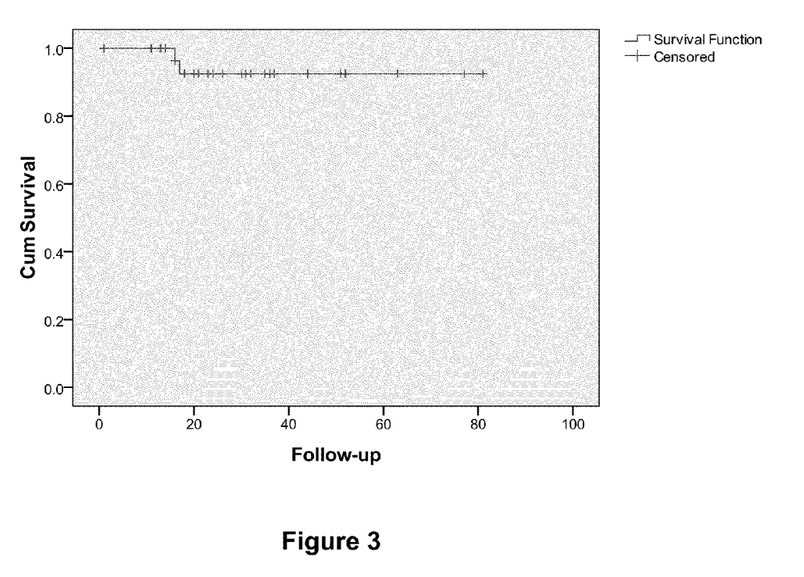
FIG. 3 shows Kaplan-Meier analysis of the good prognosis group. Follow-up time is in months and the cumulative survival function is based upon censored data for the patient population with adequate follow-up time for 31 patients with a good prognosis as determined from their score based upon 15 markers as described in "Methods for determination of overall survival (OS) prognostics"
Figure 4:
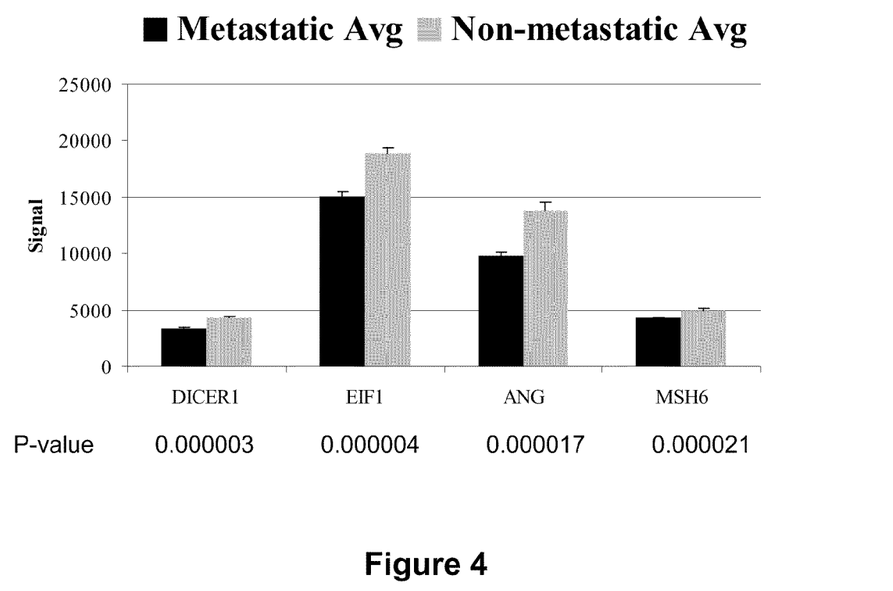
FIG. 4 shows metastatic markers. Average expression levels of probes prognostic of metastatic disease are shown for metastatic and non-metastatic cohorts of TN patients. Error bars depict the standard error within each cohort.

Kaplan-Meier survival analysis and the hazard function for the entire cohort are depicted in FIGS. 1 and 2, respectively. Kaplan-Meier analysis of the good and poor prognosis cohorts are contained in FIG. 4. Mortality events are summarized in appendix 1 and mean and median survival times are summarized in appendix 2.

APPENDIX 2

SUMMARY OF MEAN & MEDIAN SURVIVAL TIMES
Means and Medians for Survival Time

| Group | Mean$^a$ | | | | Median | | | |
|---|---|---|---|---|---|---|---|---|
| | Estimate | Std. Error | 95% Confidence Interval Lower Bound | 95% Confidence Interval Upper Bound | Estimate | Std. Error | 95% Confidence Interval Lower Bound | 95% Confidence Interval Upper Bound |
| Poor Prognosis | 51.586 | 5.092 | 41.606 | 61.567 | 67.000 | 27.691 | 12.726 | 121.274 |
| Good Prognosis | 76.127 | 3.314 | 69.632 | 82.623 | — | — | — | — |
| Overall | 63.153 | 4.200 | 54.921 | 71.386 | — | — | — | — |

$^a$Estimation is limited to the largest survival time if it is censored.

Determination of Overall Survival (OS) Prognostics: Survival data obtained from SEER was combined with expression data for 63 women with TN disease. Of these 63 patients, 13 were deceased as confirmed by SEER. Data was censored by the length of follow-up which was determined as the number of months between the diagnosis and the last contact with the patient or for those patients deceased the date of death. Average length of follow-up was 31.6 months for the entire cohort, with those patients experiencing mortality events having an average time to event of 25 months. Cox survival analysis was used to determine mRNA markers prognostic of overall survival (OS) with a false discovery rate (FDR) of less than 5% using Significance Analysis of Microarrays (SAM, Tusher et al.). In all 15 probes from 12 unique genes were found significant. These 15 probes were then used to create a classifier in which the SAM score was used to determine the weight of the probe. For each probe in each patient the expression intensity was multiplied by the weight of the probe and the total score was summed for each patient. Patients were then median bifurcated by their aggregate score and analyzed using Kaplan Meier analysis and a log-rank test to determine if differences exist in prognosis based on our classifier.

EXAMPLE 3

Identification of a 4-Gene Set that can be Used as Predictors for the Metastatic Potential of TN Breast Cancer Four probes were determined prognostic of metastatic disease, these probes map to the genes ANG, DICER1, EIF1, and MSH6. Average expression levels are graphically depicted in FIG. 4 and specific transcript sequences are contained in Table 2 (above).

Determination of Metastatic Prognostics: SEER epidemiological data contained metastatic information on 44 of the 63 TN patients. The remaining 19 patients were excluded from the metastatic analysis. Of the 44 patients with metastatic follow-up data, 6 had distant metastases. As no time to metastasis was available metastatic disease was treated as a binomial variable and expression markers were determined using a Bonferroni corrected student's t-test for heteroscedastic data (in other terms we did not make the assumption of equal variances between the two cohorts). A criterion p-value of less than 0.05 was imposed and corrected for 1,536 mRNA expression probes yielding a Bonferroni corrected p-value threshold of p<0.0000326.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

REFERENCES

Abramovitz et al., *Biotechniques* 44 (3):417-23 (2008).
Bibikova et al., *Am J Pathol* 165: 1799-1807 (2004).
Fan et al., *Genome Res* 14: 878-885 (2004).

Kreike et al., *Breast Cancer Res* 9: R65 (2007).
Sambrook et al., Molecular Cloning: A Laboratory Manual, 3rd Ed., Cold Spring Harbor Press, Cold Spring Harbor, N.Y. (2001).

---

The invention claimed is:

1. A method of treating breast cancer in a subject having a triple negative (TN) breast cancer, the method consisting of the steps:
   (a) quantifying mRNA expression level of biomarkers STK3 and KLF6, and at least one biomarker selected from CD24 and KRAS in a test sample from a subject using a biological assay;
   (b) comparing said mRNA expression level of said biomarkers selected from STK3, KLF6, and at least one of CD24 and KRAS quantified in step (a) to the expression level of said biomarkers quantified using the biological assay in a standard sample indicative of a recurrent TN breast cancer; and
   (c) administering an aggressive cancer treatment regimen to the subject based on an increase in the expression level of the biomarkers between the standard sample and the test sample.

2. The method of claim 1, wherein the sample comprises TN breast tumor tissue.

3. The method of claim 1, wherein the test sample is a frozen fixed paraffin embedded tumor sample.

4. The method of claim 1, wherein mRNA expression levels of the biomarkers are quantified with a biological assay chosen from reverse-transcription polymerase chain reaction (RT-PCR) assay, quantitative real-time-PCR (qRT-PCR), Northern analysis, microarray analysis, and cDNA-mediated annealing, selection, extension, and ligation (DASL®) assay.

5. The method of claim 4, wherein mRNA expression levels of the biomarkers are quantified with a biological assay consisting of the cDNA-mediated annealing, selection, extension, and ligation (DASL®) assay.

6. The method of claim 1, wherein the at least three biomarkers are CD24, KLF6, and STK3.

7. The method of claim 1, wherein the at least three biomarkers are KLF6, KRAS, and STK3.

* * * * *